United States Patent [19]

Parker et al.

[11] Patent Number: 5,284,972

[45] Date of Patent: Feb. 8, 1994

[54] N-ACYL-N,N',N'-ETHYLENEDIAMINETRIACETIC ACID DERIVATIVES AND PROCESS OF PREPARING SAME

[75] Inventors: Brian A. Parker, Nashua; Barry A. Cullen, Lyndeborough, both of N.H.

[73] Assignee: Hampshire Chemical Corp., Lexington, Mass.

[21] Appl. No.: 76,446

[22] Filed: Jun. 14, 1993

[51] Int. Cl.$^5$ .......................................... C07C 229/00
[52] U.S. Cl. ................................. 562/565; 544/384; 554/51
[58] Field of Search .................. 562/565; 554/51

[56] References Cited

U.S. PATENT DOCUMENTS

| | | | |
|---|---|---|---|
| 2,413,856 | 1/1947 | Bersworth | 562/565 |
| 3,313,779 | 4/1967 | White | 260/59 |
| 3,515,742 | 6/1970 | Morgan et al. | 260/465.5 |
| 3,733,355 | 5/1973 | Harris et al. | 260/534 E |
| 3,758,534 | 9/1973 | Popper et al. | 260/429 |
| 4,115,634 | 9/1978 | Bechara et al. | 521/126 |
| 4,190,571 | 2/1980 | Lai et al. | 260/45.8 |
| 4,405,531 | 9/1983 | Franz | 260/501.12 |
| 4,432,907 | 2/1984 | Wieder et al. | 562/565 |
| 4,704,465 | 11/1987 | Lannert et al. | 558/346 |
| 4,705,889 | 11/1987 | Hendricks et al. | 562/565 |
| 4,826,673 | 5/1989 | Dean et al. | 562/565 |
| 4,830,786 | 5/1989 | Pease et al. | 260/396 N |
| 4,975,418 | 12/1990 | Ungerer et al. | 562/565 |
| 4,980,502 | 12/1990 | Felder et al. | 562/565 |
| 5,191,081 | 3/1993 | Parrcer | 544/384 |

FOREIGN PATENT DOCUMENTS

| | | |
|---|---|---|
| 828547 | 7/1949 | Fed. Rep. of Germany . |
| 1337445 | 8/1962 | France . |
| 42-9564 | 4/1965 | Japan . |
| 2076806 | 12/1981 | United Kingdom . |
| 90/11996 | 10/1990 | World Int. Prop. O. . |

OTHER PUBLICATIONS

Canadian Journal of Chemicstry, 48, 163 (1970): R. M. Genik-Sas-Berezowski, et al.; Chelating Polymers I.
Abstract vol. 62, 1965 9129 38-Heterocyclic Compounds.
Abstract vol. 71, 1969 p. 451 78-Inorganic Chemicals and Reactions Chemical Abstracts vol. 92, (1980) p. 588.
Abstract vol. 67 (1967) p. 2155 36-Plastics Manufacture and Processing.
Chemical Abstracts, vol. 114, (1991) p. 362.

*Primary Examiner*—Paul J. Killos
*Attorney, Agent, or Firm*—Nields & Lemack

[57] ABSTRACT

Novel N-acyl derivatives of ethylenediaminetriacetic acid are disclosed, as well as a process for preparing the same.

5 Claims, No Drawings

N-ACYL-N',N'-ETHYLENEDIAMINETRIACETIC ACID DERIVATIVES AND PROCESS OF PREPARING SAME

BACKGROUND OF THE INVENTION

Ethylenediaminetriacetic acid (ED3A) or its salts (such as ED3ANa₃) has applications in the field of chelating chemistry, and may be used as a starting material in the preparation of strong chelating polymers, oil soluble chelants, surfactants and others. Conventional routes for the synthesis of ethylenediaminetriacetic acid were achieved via its N-benzyl derivative, which was subsequently hydrolyzed in alkaline solutions to ED3ANa₃, thus avoiding cyclization to its 2-oxo-1,4-piperazinediacetic acid (3KP) derivative. Syntheses attempted by both the alkaline condensation of chloroacetic acid with ethylenediamine, and the carboxymethylation of the diamine with formaldehyde and sodium cyanide resulted in complex mixtures requiring complex extraction techniques (e.g. almost exclusive solubility of 3KP in boiling dimethylformamide, Can. J. Chemistry 1970, 48(1), 163-175) to generate the desired product, and then in only relatively poor yield. In addition, conventional processes resulted in large quantities of by-product, such as ethylenediaminetetraacetic acid (ED4A). Where the by-products were especially objectionable, complicated blocking techniques were necessary in order to achieve a relatively pure solution.

One example of the synthesis of ethylenediamine-N,N,N'-triacetic acid is shown in *Chemical Abstracts* 78, Vol. 71, page 451, no. 18369c, 1969. There it is disclosed that ethylenediamine reacts with ClH₂CCO₂H in a 1:3 molar ratio in basic solution at 10° C. for 24 hours to form a mixture from which ethylenediamine-N,N,N'-triacetic acid can be separated by complexing the same with Co(III). The resulting cobalt complexes can be isolated through ion exchange.

These conventional processes do not produce ED3A with sufficient purity or in sufficient quantity to make the preparation of N-acyl derivatives of ED3A economically attractive. Such derivatives are desirable from the technical standpoint in view of their utility as surfactants, corrosion inhibitors, lubricant enhancers, enzyme inhibitors, metal precipitation additives, chelants, emulsifiers, etc.

Co-pending U.S. Pat. No. 5,250,728, the disclosure of which is hereby incorporated by reference, discloses a simple process for the synthesis of ED3A or its salts in high yield. Specifically, a salt of N,N'-ethylenediaminediacetic acid (ED2AH₂) is condensed with stoichiometric amounts, preferably slight molar excesses of, formaldehyde, at temperature between 0° and 110° C., preferably 0° to 65° C. and pH's greater than 7.0 to form a stable 5-membered ring intermediate. The addition of a cyanide source, such as gaseous or liquid hydrogen cyanide, aqueous solutions of hydrogen cyanide or alkali metal cyanide, in stoichiometric amounts or in a slight molar excess, across this cyclic material at temperatures between 0° and 110° C., preferably between 0° and 65° C., forms ethylenediamine N,N'-diacetic acid-N'-cyanomethyl or salts thereof (mononitrile-diacid). The nitrile in aqueous solutions may be spontaneously cyclized in the presence of less than 3.0 moles base: mole ED2AH₂, the base including alkali metal or alkaline earth metal hydroxides, to form 2-oxo-1,4-piperazinediacetic acid (3KP) or salts thereof, which is the desired cyclic intermediate. In the presence of excess base, salts of ED3A are formed in excellent yield and purity. This U.S. Pat. No. 5,250,728 also discloses an alternative embodiment in which the starting material is ED2AH$_a$X$_b$, where X is a base cation, e.g., an alkali or alkaline earth metal, a is 1 to 2, and b is 0 to 1 in aqueous solutions. The reaction mixture also can be acidified to ensure complete formation of carboxymethyl-2-oxopiperazine (the lactam) prior to the reaction. Formaldehyde is added, essentially resulting in the hydroxymethyl derivative. Upon the addition of a cyanide source, 1-cyanomethyl-4-carboxymethyl-3-ketopiperazine (mononitrile monoacid) or a salt thereof is formed. In place of CH₂O and a cyanide source, HOCH₂CN, which is the reaction product of formaldehyde and cyanide, may also be employed in this method. Upon the addition of any suitable base or acid, this material may be hydrolyzed to 3KP. The addition of a base will open this ring structure to form the salt of ED3A.

U.S. Pat. Nos. 5,177,243 and 5,191,081, the disclosures of which are incorporated herein by reference, disclose various intermediates in the aforementioned syntheses.

In view of this relatively new technology, ethylenediaminetriacetic acid now can be readily produced in bulk and high yield.

It is therefore an object of the present invention to produce N-acyl derivatives of ethylenediaminetriacetic acid in high conversions and excellent yield.

SUMMARY OF THE INVENTION

The problems of the prior art have been overcome by the instant invention, which provides novel N-acyl derivatives of ethylenediaminetriacetic acid, and a process for preparing the same.

DETAILED DESCRIPTION OF THE INVENTION

The production of N-acyl derivatives of ethylenediaminetriacetic acid in accordance with the present invention can be accomplished according to the following general reaction scheme:

It will be readily understood by those skilled in the art that the starting ED3A derivative can be the acid itself, or suitable salts thereof, such as alkali metal and alkaline earth metal salts, preferably sodium or potassium salts.

Saturated N-Acyl ED3A derivatives that are the product of the foregoing reaction can be represented by the following chemical formula:

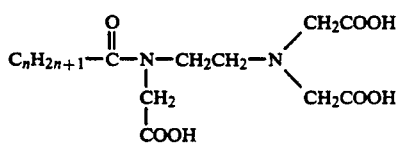

wherein n is from 1 to 40. Where unsaturation occurs, the structure may be shown as follows:

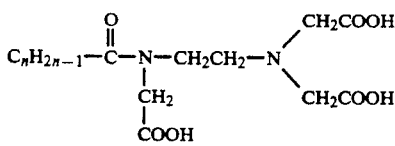

where n is from 2 to 40. As unsaturation increases, the formulae are:

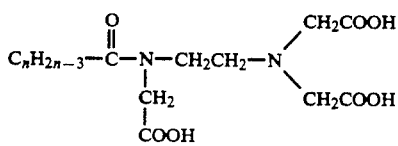

where n is 3 to 40;

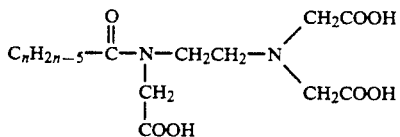

where n is 4 to 40; and

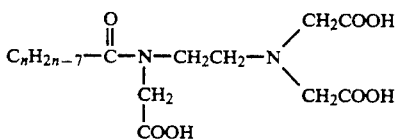

where n is 5 to 40, etc.

Those skilled in the art will recognize that any acyl chloride can be used in the foregoing reaction scheme, including pentanoyl, hexanoyl, heptanoyl, octanoyl, nananoyl, decanoyl, lauroyl, myristoyl, palmitoyl, oleoyl, stearoyl and nonanoyl. The present invention also encompasses branched acyl chlorides, such as neopentanoyl, neoheptanoyl, neodecanoyl, iso-octanoyl, isonananoyl and iso-tridecanoyl, as well as aromatic acyl groups, such as benzoyl and napthoyl. The fatty acid chains may be substituted, such as by one or more halogen and/or hydroxyl groups. Examples of hydroxy-substituted fatty acids including ipurolic (3,11-dihyroxytetradecanoic), ustilic (2,15,16-trihydroxyhexadecanoic), ambrettolic (16-hydroxy-7-hexadecanoic), ricinoleic (12-hydroxy-cis-9-octadecenoic), ricinelailic (12-hydroxy-trans-9-octadecenoic), 9,10-dihydroxyoctadecanoic, 12-hydroxyoctadecanoic, kalmlolenic (18-hydroxy-8,11,13-octadecatrienoic),ximenynolic(8-hydroxy-trans-11-octadecene-9-ynoic),isanolic(8-hydroxy-17-octadecene-9,11-diynoic)and lequerolic)14-hydroxy-cis-11-eicosenoic), as well as acyl chlorides of the above (the above named derivatives wherein the suffix "oic" is replaced by "oyl chloride"). Suitable halogen-substituted fatty acids include trifluoromethylbenzoyl chloride, pentadecafluorooctanoyl chloride, pentafluoropropionoyl chloride, pentafluorobenzoyl chloride, perfluorostearoylchloride, perfluorononamoylchloride, perfluoroheptanoylchloride and trifluoromethylacetyl chloride.

Poly N-acyl ethylenediaminetriacetic acid derivatives, such as dicarboxylic acid derivatives having the following general formula also can be produced in accordance with the instant invention:

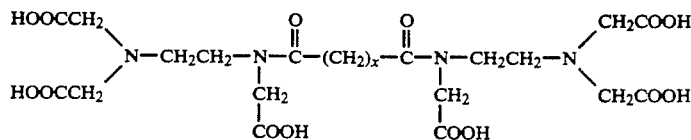

or:

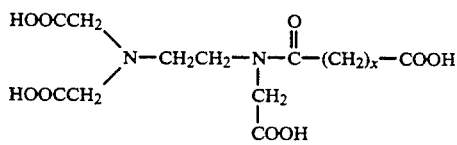

where x is 1 to 40. Specific examples include mono and di ED3A derivatives such as oxalyldi ED3A, oxalylmono ED3A, maleylmono ED3A, maleyldi ED3A, succinoylmono ED3A, succinoyldi ED3A, etc.

Preferably the ED3A acid or salt of ED3A, such as the trisodium or tripotassium salt, used as the starting material in the instant invention is prepared in accordance with the process disclosed in the aforementioned U.S. Pat. No. 5,250,728. Specifically, the alkaline condensation of formaldehyde with N,N-bis(carboxymethyl)imidazolidine is carried out:

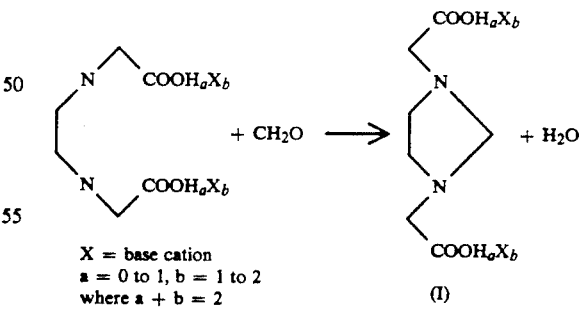

X = base cation
a = 0 to 1, b = 1 to 2
where a + b = 2    (I)

The reaction may be carried out in the presence of additional base, such as alkali and alkaline earth metal hydroxides, preferably sodium or potassium hydroxide. Compound (I) is the bridged reaction product of EDDANa$_{(1.0 \to 2.0)}$ and formaldehyde, which is a stable intermediate. Compound (I) is formed easily between 0° and 110° C., and the reaction proceeds quickly at pH's greater than about 7.0. Compound (I) is then reacted with cyanide as follows:

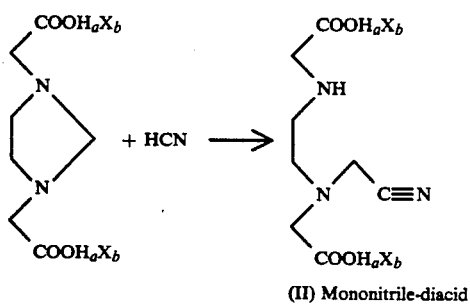

(II) Mononitrile-diacid

Compound (II) is readily formed at temperatures between 0° and 110° C., most preferably between about 15° to 65° C. to enhance the reaction rate. Suitable sources of cyanide include gaseous hydrogen cyanide, an aqueous solution of hydrogen cyanide, or alkali metal cyanide such as sodium cyanide or potassium cyanide, etc. The cyanide may be used in stoichiometric amounts, although slight molar excesses may be used, preferably 0.5%–2.0%. Compound (II) is then hydrolyzed to the monoamide-diacid (compound (III), partially hydrolyzed mononitrilediacid) and its spontaneous cyclization to 3KP:

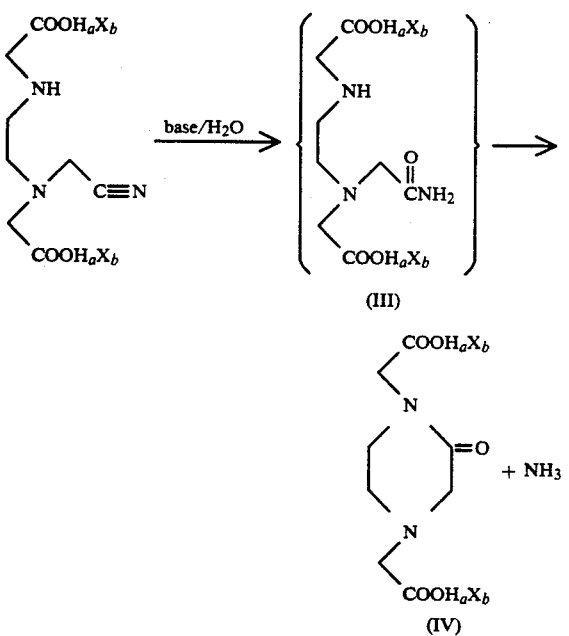

Compound (IV) forms readily in the presence of a base such as alkali metal or alkaline earth metal hydroxides. Preferably the base is NaOH. Mole ratios of <3.0M base:1M ED2AH$_2$ but preferably <2.0M base: 1M ED-2AH$_2$ are employed. Higher concentrations of base (i.e., >3.0M base: 1M ED2AH$_2$) cause some disproportionation of the diacid mononitrile and some ED4A is formed, especially at temperatures >65° C. When the mole ratio of base to ED2A is <2.0, higher temperatures may be used. Ammonia is eliminated between an amide group and an imino group on the same molecule. However, at lower temperatures (<65° C.) higher amounts of base may be employed (>2.0M) and hydrolysis of compound (II) can proceed directly to ED3A without cyclization. The last step in the formation of ED3A is the hydrolysis of 3KPNa$_2$ by at least the addition of 1 equivalent of caustic, preferably a 1 molar excess of caustic. This amounts to approximately 5% weight excess (free) caustic in solution on a 40% ED-3ANa$_3$ solution. The solution is boiled under atmospheric pressure to the desired concentration. Preferably the reaction is carried out by raising the temperature from the temperature in the previous step to the boil over a period from about 30 minutes to about 6 hours. The resulting solutions typically give approximately 35–40% ED3ANa$_3$, with approximately 2% 3KPNa$_2$ remaining as an unopened ring structure. This corresponds to about 94% conversion to ED3ANa$_3$, with the remaining 6% of mass existing as 3KPNa$_2$.

Alternatively, the starting material for preparation of ED3A is ED2AH$_a$X$_b$, where x is a base, e.g., an alkali or alkaline earth metal base, a is 1 to 2, and b is 0 to 1 in aqueous solutions. The reaction mixture also can be acidified with acids having pK$_a$'s less than or equal to 3, prior to, during or after the addition of a cyanide source, to ensure complete formation of carboxymethyl-2-oxopiperazine (the lactam). Formaldehyde is added, essentially resulting in the hydroxymethyl derivative. Upon addition of the cyanide source, 1-cyanomethyl-4-carboxymethyl-3-ketopiperazine or salt thereof is formed, and can be isolated in good yield in crystalline form by conventional means after cooling the reaction mixture. Glycolonitrile can be used in place of formaldehyde and the cyanide source. Upon the addition of any suitable base or acid, this material may be hydrolyzed to 3KP. The addition of base (>2.0 equivalents but preferably greater than or equal to 3.0 equivalents) will open this ring structure to form the salt of ED3A. Heating the reaction mixture will enhance the rate of reaction. The overall reaction scheme is shown below:

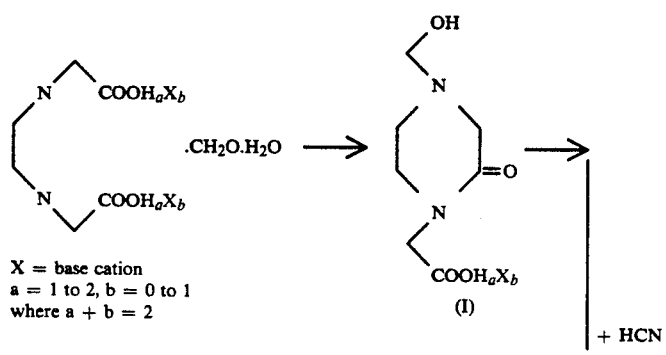

X = base cation
a = 1 to 2, b = 0 to 1
where a + b = 2

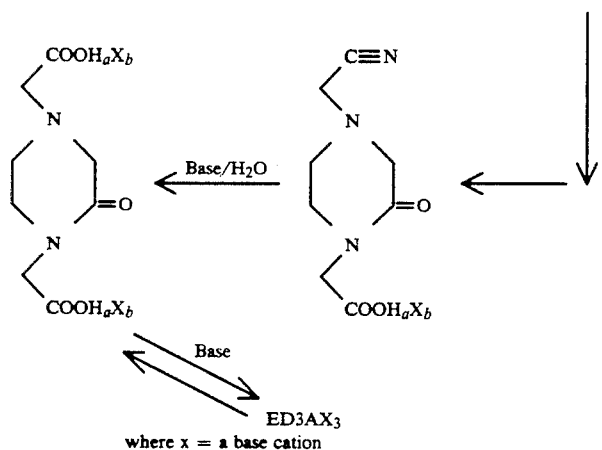

where x = a base cation

In a further embodiment for producing ED3A, EDDA is allowed to form the lactam (carboxymethyl-2-oxo-piperazine) by acidification, and the lactam is reacted with chloro or bromo acetic acid to form ED3A or 3KP.

Regardless of which of the above embodiments is used to derive the starting material for the instant process, the resulting ED3A derivative need not be isolated from the reaction solution prior to reaction with the fatty acid in accordance with the present invention.

Where the N-acyl ED3A acid is produced, it can be readily converted into salts by partial or complete neutralization of the acid with the appropriate base. The acid also can be produced from N-acyl ED3A salts by neutralization of the base with a quantitative amount of acid.

The reaction temperature is not particularly critical, and can be in a range from about 0° C. to about 100° C., preferably between about 10° C. and about 80° C., most preferably between about 20° and 50° C. Upon the addition of the fatty acid chloride, the exotherm which is produced can be used to heat the reaction solution. Preferably the reaction is conducted in the presence of sufficient caustic to prevent cyclization of ED3A due to the elimination of HCl. Suitable caustic includes NaOH and KOH. Preferably the pH of the reaction solution is maintained at about 10; pH's of about 9 or less have been found to result in excessive cyclization of ED3A. If excessive cyclization does occur, ED3A can be regenerated by the further addition of caustic.

Preferably the reactants are used in near stoichiometric amounts, although an excess of ED3A or the acyl chloride can be used where desired. Alcohols such as isopropyl alcohol, methanol and ethanol can be used as solvents for the reaction system.

In the following examples, all ED3ANa$_3$ solutions referred to contained 1 free mole of NaOH per mole of ED3ANa$_3$. In Examples 3-5, a 100% molar excess of ED3A was employed to ensure complete reaction.

EXAMPLE 1

22.4 g of 98% lauroyl chloride were added to 111 g of trisodium salt of ethylenediaminetriacetic acid (27%), with vigorous stirring. Prior to the addition of the lauroyl chloride, 20 g of isopropyl alcohol was added to the ED3ANa$_3$ solution. The reaction mix exothermed to 55° C. upon the addition of the fatty acid chloride. The solution was analyzed by HPLC and 0.04 moles of the fatty acid chloride were found to react to produce 0.04M of free fatty acid, as lauric acid.

EXAMPLE 2

20 g of lauroyl chloride (98%) was added dropwise over 10 minutes to a 115 g ED3ANa$_3$ (27%) solution to which 20 g of isopropyl alcohol was added prior to the lauroyl chloride addition, with vigorous stirring. The temperature was maintained at 20° C. throughout the reaction. Twelve hours later the sample was analyzed for free lauric acid by HPLC, and 0.2M of lauric acid were found, indicating relatively high conversion to lauroyl ED3ANa$_3$.

EXAMPLE 3

20 g of isopropyl alcohol were added to 157.8 g of a 38% ED3ANa$_3$ solution. 17.7 g of nonanoyl chloride were added dropwise over 10 minutes to the ED3ANa$_3$ solution with vigorous stirring. The temperature prior to the addition was 25° C. and on completion of the fatty acid chloride addition was 35° C. The solution was stirred for 35 minutes and acidified to a pH of 4.3 with sulfuric acid. The solution split into two layers.

EXAMPLE 4

20 g of isopropyl alcohol were added to 158 g of a 38% ED3ANa$_3$ solution. 30.1 g of oleoyl chloride were added to the ED3A solution dropwise with vigorous stirring over approximately 10 minutes. During the reaction, the viscosity of the solution began to increase and stirring became difficult. Therefore, 50 g of H$_2$O were added to the reaction to help thin the solution and allow for easier mixing. The solution was allowed to stir overnight, and was then acidified to a pH of 2.5 with H$_2$SO$_4$. An emulsion was formed, which appeared to break upon further dilution with 100 g of H$_2$O, and a light waxy white solid was filtered off.

EXAMPLE 5

20 g of isopropyl alcohol were added to 158 g of a 38% solution of ED3ANa$_3$. 24.7 g of myristoyl chloride were added dropwise over 15 minutes. The solution was stirred for 1 hour. More isopropyl alcohol/H$_2$O (50/50 wt/wt) was added to prevent the solution from gelling, based on visual observation. The solution was acidified to a pH of approximately 2.5 with H$_2$SO$_4$, and a white waxy solid was filtered off.

EXAMPLE 6

18 g of isopropyl alcohol were added to a 144 g of a 25% solution of ED3ANa$_3$. 26.3 g of lauroyl chloride were pumped into the solution of ED3ANa$_3$ uniformly over 20 minutes by means of a metering pump. The temperature of the reaction mixture was maintained at 30° C. throughout the addition. The solution was stirred at 30° C. for another 30 minutes after the lauroyl chloride addition was complete. The solution was then acidified with 18.4 g of 96% H$_2$SO$_4$ and heated to approximately 80° C. The reaction mass was then transferred to a 500 ml. jacketed separatory funnel and held at 80° C. for 30 minutes. The contents separated into two layers. 94.8 g were recovered from the organic layer and was found to contain 3.84% lauric acid by HPLC. The bottom layer was discarded. Further analysis of the organic layer by HPLC confirmed that lauroyl ED3AH$_3$ was indeed synthesized.

EXAMPLE 7

Example 6 was repeated except that the reaction temperature was maintained at 40° C. During acidification, 22.66 g of 96% H$_2$SO$_4$ were used. The weight of the organic layer recovered was 68.8 g and was found to contain 4.49% lauric acid.

EXAMPLE 8

Example 7 was repeated except that the reaction temperature was maintained at 50° C. The weight of the organic layer recovered was 67.1 g containing 11.34% lauric acid.

In all of the above examples, the product isolated was confirmed to consist primarily of N-acyl ED3AH$_3$ and some free fatty acid, or salts thereof. Solid samples, in the acid form, were recrystallized from isopropyl alcohol and isooctane to remove the free fatty acid. Analysis of the recrystallized materials by NMR confirmed the N-acyl ED3A structures. Analysis by HPLC for free fatty acid on these recrystallized samples were all found to be well below the detection point of approximately 0.1% fatty acid.

What is claimed is:

1. N-acyl ethylenediaminetriacetic acid or salts thereof, wherein said acyl group is a straight or branched aliphatic or aromatic group containing from 1 to 40 carbon atoms.

2. The N-acyl ethylenediaminetriacetic acid or salts of claim 1, wherein said acyl group is a derivative of a carboxylic acid and contains 1 to 40 carbon atoms.

3. Poly N-acyl ethylenediaminetriacetic acid or salts thereof, wherein said acyl group is a straight or branched aliphatic or aromatic group containing from 1 to 40 carbon atoms.

4. A process for producing an N-acyl ethylenediaminetriacetic acid or salt thereof, wherein said acyl group is a straight or branched aliphatic or aromatic group containing from 1 to 40 carbon atoms, said process comprising reacting ethylenediaminetriacetic acid or its salt with said acyl group in the presence of sufficient caustic to minimize cyclization of said ethylenediaminetriacetic acid or salt.

5. A process for producing an N-acyl ethylenediaminetriacetic acid, comprising:
   a. reacting formaldehyde with an alkali metal or alkaline earth metal salt of ethylenediaminediacetic acid;
   b. reacting the product of step a with a cyanide source;
   c. allowing for the spontaneous cyclization of the resulting monoamide-diacid;
   d. reacting the cyclization product of step c with at least 1 equivalent of alkali metal or alkaline earth metal hydroxide; and
   e. reacting the product of step d with an acyl group having from 1 to 40 carbon atoms.

* * * * *